United States Patent [19]

Sach

[11] Patent Number: 4,863,936

[45] Date of Patent: Sep. 5, 1989

[54] 3,5-SUBSTITUTED-2-PYRIDYL-ALKYLAMINOCYCLOBUTENEDIONES HAVING HISTAMINE $H_1$-ANTAGONIST ACTIVITY

[75] Inventor: George S. Sach, Welwyn, England

[73] Assignee: Smith Kline & French Laboratories Limited, Welwyn Garden City, England

[21] Appl. No.: 921,186

[22] Filed: Oct. 21, 1986

Related U.S. Application Data

[62] Division of Ser. No. 735,011, May 17, 1985, Pat. No. 4,640,926, which is a division of Ser. No. 559,520, Dec. 9, 1983, Pat. No. 4,532,252.

[51] Int. Cl.[4] .................... A61K 31/44; C07D 213/75; C07D 213/61; C07D 213/36

[52] U.S. Cl. .................... 514/332; 514/335; 514/338; 514/349; 514/351; 514/352; 514/357; 546/261; 546/264; 546/265; 546/292; 546/297; 546/300; 546/307; 546/308; 546/309; 546/312; 546/334; 546/336; 546/337

[58] Field of Search .................... 544/8, 320; 546/256, 546/277, 281, 284, 304, 307, 329, 345, 270, 261, 264, 265, 292, 309, 336, 308, 334, 297, 300, 312, 3373; 514/222, 272, 333, 342, 343, 332, 349, 357, 335, 351, 338, 352

[56] References Cited

U.S. PATENT DOCUMENTS 4,539,316 9/1985 Algieri et al. .................... 514/332

Primary Examiner—John M. Ford
Attorney, Agent, or Firm—Linda E. Hall; Janice E. Williams; Alan D. Lourie

[57] ABSTRACT

Various substituted aminoalkylamino-2-pyridine derivatives are disclosed which are useful as histamine $H_1$-antagonists.

10 Claims, No Drawings

3,5-SUBSTITUTED-2-PYRIDYL-ALKYLAMINOCY-CLOBUTENEDIONES HAVING HISTAMINE H₁-ANTAGONIST ACTIVITY

This is a divisional of application Ser. No. 735,011 filed May 17, 1985, now U.S. Pat. No. 4,640,926 which is a division of Ser. No. 559,520 filed Dec. 9, 1983, now U.S. Pat. No. 4,532,252.

This invention relates to certain pyridine derivatives, a process for their preparation, compositions containing they and their use as histamine $H_1$-antagonists.

Histamine, a physiologically active compound endogenous in mammals, exerts its action by interacting with certain sites called receptors. One type of receptor is known as a histamine $H_1$-receptor (Ash and Schild, Brit. J. Pharmac. 1966, 27, 427) and the actions of histamine at these receptors are inhibited by drugs commonly called "antihistamines" (histamine $H_1$-antagonists) a common example of which is mepyramine. A second type of histamine receptor is known as the $H_2$-receptor (Black et al Nature 1972, 236, 385). The actions of histamine at these receptors are not inhibited by mepyramine but are inhibited by burimamide. Compounds which inhibit the actions or histamine at histamine $H_2$-receptors are called histamine $H_2$-antagonists.

A group of compounds has now been discovered which have a relatively higher level of $H_1$- to $H_2$-antagonist activity. These compounds are useful as histamine $H_1$-antagonists, that is, for the treatment of diseases for example bronchial asthma, rhinitis, hayfever and allergic eczema whose symptoms are mediated through the action of histamine at $H_1$-receptors.

According to the present invention there is provided compounds of formula (1):

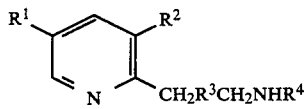

and pharmaceutically acceptable salts thereof;
where
$R^1$ is halogen, nitro, amino (or a pharmaceutically acceptable derivative of the amino group which is convertible in vivo into amino) or $C_{1-4}$ alkyl;

$R^2$ is halogen, nitro, amino (or a pharmaceutically acceptable derivative of the amino group which is convertible in vivo into amino), $C_{1-4}$ alkyl or $C_{3-4}$ alkoxy;

$R^3$ is a $C_{1-3}$ alkylene group; and $R^4$ is a group of formula (2):

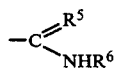

where
$R^5$ is NCN, NNO₂, NH or CHNO₂ and $R^6$ is hydroxy, amino, $C_{1-6}$a optionally substituted phenyl- or pyridyl(-$C_{1-6}$)alkyl (the optional substituents being one or more $C_{1-6}$ alkyl, or $C_{1-6}$ alkoxy groups or halogen atoms or a methylenedioxy group); or $C_{2-4}$ alkynyl;

or $R^4$ is a group of formula (3):

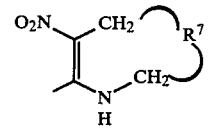

where
$R^7$ is a covalent bond or methylene or ethane-1, 2-diyl optionally substituted with one $C_{1-6}$ alkyl group and a second $C_{1-6}$ alkyl group or a phenyl-($C_{1-6}$)alkyl group;

or a group of formula (4):

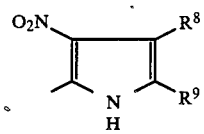

where
$R^8$ is hydrogen; $C_{1-6}$ alkyl; optionally substituted phenyl or phenyl($C_{1-6}$)alkyl, (the substituents being one or more $C_{1-6}$ alkyl or $C_{-6}$ alkoxy groups or halogen atoms or a methylenedioxo group) of optionally substituted pyridyl or pyridyl($C_{-6}$,alkyl, the optional substituents being one or more $C_{-6}$ alkyl groups or $C_{1-6}$ alkoxy groups or halogen atoms; and $R^9$ or $C_{-6}$ alkyl groups or halogen atoms; and $R^9$ is hydrogen or $C_{1-6}$ alkyl;

or a group of formula (5):

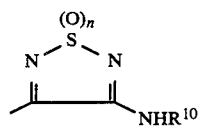

where
n is 0, 1 or 2

$R^{10}$ is hydrogen, $C_{1-6}$ alkyl, or optionally substituted phenyl or phenyl($C_{1-6}$)alkyl (the substituents being one or more $C_{1-6}$ alkyl, or $C_{-6}$ alkoxy groups or halogen atoms(; or a methylenedioxy group or optionally substituted pyridyl or pyridyl($C_{-6}$)-alkyl where the optional substituents are one or more $C_{1-6}$ alkyl or $C_{-6}$ alkoxy groups or halogen atoms;

or a group of formula (6):

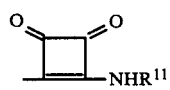

where
$R^{11}$ is hydrogen, $C_{1-6}$ alkyl, optionally substituted phenyl or phenyl($C_{1-6}$)alkyl, (the substituents being one or more $C_{1-6}$ alkyl or $C_{1-6}$ alkoxy groups or halogen atoms or a methylenedioxy group); optionally substituted pyridyl or pyridyl ($C_{1-6}$)alkyl, the optional substituents being one or more $C_{1-6}$ alkyl groups or $C_{1-6}$ alkoxy groups or halogen atoms;

or a group of formula (7):

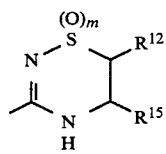

where
R$^{12}$ is hydrogen or C$_{1-6}$ alkyl, R$^{15}$ is hydrogen or together with R$^{12}$ is a fused benzene ring and
m is 0, 1 or 2
or a group of formula (8):

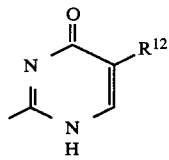

where
R$^{12}$ is hydrogen or C$_{1-6}$ alkyl.

R$^1$ and R$^2$ can represent any one of the halogens, fluorine, chlorine, bromine or iodine.

Preferably R$^1$ is halogen particularly bromine.

R$^1$ and R$^2$ can represent amino or a pharmaceutically acceptable derivative thereof which is convertible in vivo into amino, that is derivatives which in vivo are hydrolysed or metabolised into a free amino group. Examples include C$_{1-4}$ alkylamino particularly methylamino and C$_{1-4}$ alkanoylamino particularly acetamido methylamino. Examples of C$_{1-4}$ alkyl groups for R$^1$ and R$^2$ are methyl, ethyl, n-propyl, iso-propyl, n-butyl and t-butyl.

Examples of C$_{3-4}$ alkoxy groups for R$^2$ n-propoxy and n-butoxy.

Preferably R$^2$ is either C$_{-4}$ alkyl, particularly methyl or amino.

By way of example R$^3$ can be methylene, 1,2-ethanediyl, or 1,3-propanediyl.

When R$^4$ is a group of formula (2), preferably R$^5$ is NCN.

Examples of C$_{1-6}$ alkyl groups which R$^6$ to R$^{12}$ represents are methyl, ethyl and n-propyl.

Examples of substituted phenyl groups and the substituted phenyl moiety of the phenyl(C$_{1-6}$)alkyl groups for R$^6$, R$^8$, R$^{10}$ and R$^{11}$ are 3-methylphenyl, 3-methoxyphenyl, 3-chlorophenyl, 4-methylphenyl, 4-methoxyphenyl and 3,4-dimethoxyphenyl.

Examples of optionally substituted pyridyl(C$_{-6}$)-alkyl groups for R$^6$, R$^8$, R$^{10}$ and R$^{11}$ are optionally substituted 2-pyridyl-, 3-pyridyl-, or 4-pyridyl-(C$_{1-6}$)alkyl groups, and particularly 3-pyridyl-, 6-methyl-3-pyridyl- and 6-methoxy-3-pyridyl-(C$_{1-6}$)alkyl.

Particular phenyl(C$_{1-6}$)alkyl groups for R$^6$ are benzyl, 2-phenylethyl and 3-phenyl propyl.

Preferably R$^6$ is 3-pyridylmethyl or 4-pyridylmethyl.

When R$^4$ is a group of formula (3) it will be appreciated that where R$^7$ bears two substituents, these will be selected for stereochemical compatibility.

Examples of specific values for R$^7$ are methylene, ethane-1,1-diyl and ethane-1,2-diyl.

Preferably R$^7$ is methylene.
Preferably R$^8$ is hydrogen.
Preferably R$^9$ is hydrogen.
When R$^4$ is a group of formula (5), n is preferably 1.

One particular C$_{1-6}$ alkyl group for R$^{10}$ is methyl. One particular pyridyl(C$_{1-6}$)alkyl group for R$^{10}$ is 3-pyridylmethyl.

Preferably R$^{11}$ is hydrogen, methyl, benzyl, or 3-pyridylmethyl.

Preferably R$^{12}$ is hydrogen.

Preferably R$^4$ is a group of formula (5) where R$^{10}$ is hydrogen and n is 1 or a group of formula (7) where m is 2, or a group of formula (8) where R$^{12}$ is hydrogen.

Examples of particular compounds within the scope of this invention are:

N-Cyano-N'-methyl-N''-[4-(5-bromo-3-methylpyrid-2-yl)-butyl]-guanidine;

N-cyano-N'-(pyrid-3-yl-methyl)-N''-[4-(5-bromo-3-methylpyrid-2-yl)-butyl]-guanidine;

N-Cyano-N'-(pyrid-4-yl-methyl)-N''-[4-(5-bromo-3-methylpyrid-2-yl)-butyl]-guanidine;

3-[4-(5-Bromo-3-methylpyrid-2-yl)-butylamino]-4-amino-1,2,5-thiadiazole-1-oxide

3-[4-(5-Bromo-3-methylpyrid-2-yl)-butylamino]-1,2,4-dihydrothiadiazine-1,1 dioxide;

and their pharmaceutically acceptable salts.

Examples of pharmaceutically acceptable acid addition salts of compounds of formula (1) are those formed with hydrochloric, hydrobromic, sulphuric, phosphoric, acetic, citric, maleic, lactic, ascorbic and methanesulphonic acids.

Compounds of formula (1) where R$^4$ is a group of formula (2) as previously defined can be prepared by a process which comprises reacting a compound of formula (9):

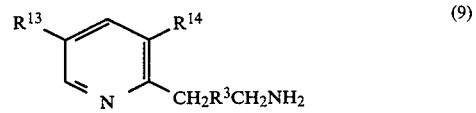

where R$^{13}$ is a group R$^1$ or a protected amino group, R$^{14}$ is a group R$^2$ or a protected amino group, R$^1$ and R$^3$ are as defined with reference to formula (1) with a compound of formula (10):

where B$^1$ is a group displaceable by amine, B$^2$ is a group displaceable with amine or is NHR$^6$ [where R$^6$ is as defined with reference to formula (2)], and B$^3$ is a group R$^5$ as defined with reference to formula (1) or NCO$_2$C$_6$H$_5$ and where B$^2$ is a group displaceable by amine reacting with an amine of formula (11):

where R$^6$ is as defined with reference to formula (1) and where B$^3$ is NCO$_2$C$_6$H$_5$ and optionally when B$^3$ is NCN, converting the group into NH.

Compounds of formula (1) where R$^4$ is a group of formula (3) or (4) can be prepared by reacting an amine of formula (9) as previously defined with a compound of formula (12) or (13):

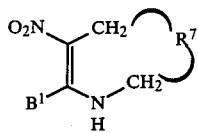
(12)

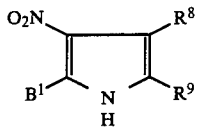
(13)

where $B^1$ is as defined with reference to formula (10).

Compounds of formula (1) where $R^4$ is a group of formula (5) can be prepared by reacting a compound of formula (9) with a compound of formula (14):

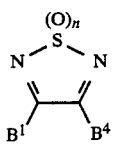
(14)

where n is as defined with reference to formula (1), $B^1$ is as defined with reference to formula (10) and $B^4$ is a group displaceable with amine or a group $NHR^{10}$, and where $B^4$ is a group displaceable with amine reacting with a compound of formula (15):

$$R^{10}NH_2 \quad (15)$$

where $R^{10}$ is as defined with reference to formula (5).

Compounds of formula (1) where $R^4$ is a group of formula (6) can be prepared by reacting a compound of formula (9) as previously defined with a compound of formula (16):

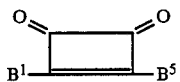
(16)

where $B^1$ is as defined with reference to formula (10) and $B^5$ is a group displaceable by amine or a group $NHR^{11}$ as defined with reference to formula (6), and where $B^5$ is a group displaceable by amine, reacting with a compound of formula (17):

$$R^{11}NH_2 \quad (17)$$

where $R^{11}$ is as defined with reference to formula (6).

Compounds of formula (1) where $R^4$ is a group of formula (7) or formula (8) can be prepared by reacting a compound of formula (9) with a compound of formula (18) or formula (19):

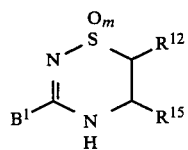
(18)

-continued

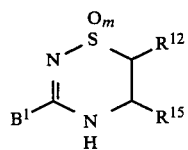
(19)

where $B^1$ is as defined with reference to formula (10) and m is as defined with reference to formula (7).

In the compound of formula (9) the protecting group in the protected amino group $R^{13}$ or $R^{14}$ can be any standard amino protecting group which is stable under the reaction conditions. For example it can be $C_{1-4}$ alkanoyl, benzyl or benzoyl. These protecting groups can be introduced and removed by standard methods.

Where the protecting group is one which is either not pharmaceutically acceptable or not convertible in vivo into amino then it is removed. Where the protecting group is convertible in vivo into amino then it need not be removed unless the free amino compound is required. Optionally any free amino group is converted into a derivative which is convertible in vivo into a free amino group. This conversion can be carried out by standard methods for example acylation or alkylation.

Examples of leaving groups displaceable by amines are where $B^1$, $B^2$, $B^4$ or $B^5$ are QS—, QSO—, QSO$_2$—, or QO (Q being $C_{1-6}$ alkyl, aryl or aralkyl). Where $B^1$, $B^2$ or $B^4$ are QO—, Q is preferably phenyl. Preferably the group $B^1$ is QS— where Q is methyl. When $B^2$ is also a group displaceable by amine, preferably it is QSO where Q is methyl. In formula (16) $B^1$ (and $B^5$ when it is a group displaceable by amine) is preferably QO where Q is methyl or phenyl.

The displacement reactions described above are preferably carried out in the presence of a solvent, for example, a $C_{1-6}$ alkanol, at elevated temperatures for example the boiling point of the reaction mixture.

Compounds of formula (9) are known or can be made by analogy with known processes as described for example in U.S. Pat. No. 4,486,434 and 4,444,772.

Compounds of formula (9) where one of $R^{13}$ and $R^{14}$ is amino and neither is nitro can also be prepared as described in U.K. Patent Application No. 8309481 as follows:

A compound of formula (20) or (21):

$$\text{NO}_2\!\!-\!\!\!\!\!\!\!\!\bigcirc\!\!\!\!\!\!\!\!-\!\!R^{13} \quad (20)$$

$$R^{14}\!\!-\!\!\!\!\!\!\!\!\bigcirc\!\!\!\!\!\!\!\!-\!\!\text{NO}_2 \quad (21)$$

where $R^3$ is $C_{1-3}$ alkylene, $R^{13}$ is halogen, $C_{1-4}$ alkyl or $C_{3-4}$ alkoxy and is halogen or $C_{1-4}$ alkyl, is reacted with hydrazine and a transition metal catalyst to produce a compound of formula (22) or (23):

$$\text{NH}_2\!\!-\!\!\!\!\!\!\!\!\bigcirc\!\!\!\!\!\!\!\!-\!\!R^{13} \quad (22)$$

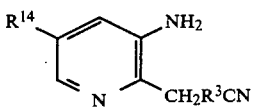

where $R^3$, $R^{13}$ and $R^{14}$ are as defined with reference to formula (20) and (21) and thereafter reacting the compound of formula (22) or (3) so obtained with more hydrazine and Raney nickel.

This reaction is carried out at a moderate temperature, for example from 5° C. to about 70° C. and preferably from about 10° C. to room temperature.

The first hydrazine reduction to prepare compounds of formula (22) or (23) can be carried out using hydrogenation catalysts which are milder than Raney nickel.

An example of a mild catalyst for this step is palladium on an inert support (in particular palladium on charcoal). The temperature at which the reaction is carried out depends on the catalyst. Where a mild catalyst is used, higher temperatures for example from 55°–70° C. may be employed. With a more powerful catalyst, for example Raney nickel, the temperature does not in practice exceed 55° C.

Preferably the reaction is carried out at from 5° C. to room temperature regardless of the catalyst.

After the first step has been carried out, the compound of formula (22) or (23) can be recovered by removing the catalyst (e.g. by filtration) and evaporating the solvent. The second stop can then be carried out by redissolving the compound of formula (22) or (23) so obtained in the same or a different solvent and reacting with Raney nickel and more hydrazine.

Preferably the reaction is carried out as a concerted process, that is by reacting the compound of formula (20) or (21) with sufficient hydrazine and a catalyst to form a compound of formula (22) or 23) in situ, where the catalyst for the first step is not Raney nickel, removing the catalyst (e.g. by filtration) and then adding Raney nickel and sufficient hydrazine to convert the compound of formula (22) or (23) into the corresponding compound of formula (9).

The reaction of the first or second step can be carried out in the presence of a solvent the choice of which is not critical to the success of the reaction provided that it is substantially inert to the reagents and product. Examples of solvents for use in this process include $C_{1-6}$ alkanols in particular methanol and ethanol.

The time for which the reaction in each step is allowed to proceed depends upon the nature of reagents, the temperature at which it is carried out and in the first step, the catalyst. The progress of the reaction can be monitored by standard techniques for example thin layer chromatography, and when the reaction has finished, the product can be isolated by standard techniques, for example removing the catalyst by filtration and evaporating the solvent.

Compounds of formula (20) and (21) can be made by analogy with known processes.

Compounds of formulae (10), (11), and (15) are known or can be made by analogy with known processes.

Compounds of formulae (12) and (13) can be made as described in U.S. Pat. Nos. 4,359,466 and 4,307,104; line 26, change "U.K. patent application No. 2067987A" U.S. Pat. No. 4,374,248.

Compounds of formula (14) can be prepared as described in U.K. Patent Application No. 2067987A.

Compounds of formula (16) can be made as described in U.S. Pat. No. 4,062,863.

Compounds of formula (17) and formula (18) are known particularly where $B^1$ is $C_{1-6}$-alkylthio (especially methylthio) and can be made as described in U.S. Pat. No. 3,932,644 and Bull Soc. Chim. France 1973 985.

The histamine $H_1$-antagonist activity of the compounds of formula (1) can be demonstrated in vitro in the guinea pig ileum test. In this test an isolated portion of the guinea pig ileum is secured under tension (500 mg) between an anchorage and a transducer in a 10 ml tissue bath and immersed in magnesium free Tyrode solution with constant aeration at a temperature of 30° C. The output from the transducer is amplified. The amplified output is in turn fed to a flat bed recorder. Measured amounts of histamine are added to the tissue bath so that the histamine concentration increases step-wise until the force of the contraction reaches a maximum. The tissue bath is washed out and filled with fresh magnesium free Tyrode solution containing compound under test. The solution is left in contact with the tissue for 8 min. and measured amounts of histamine are added again until a maximum contraction is recorded. The assay is repeated with increasing concentrations of test compound and the dose of histamine giving 50% of maximum contraction is noted. A dose ratio (DR) was calculated by comparing the concentrations of histamine required to produce 50% maximum response in the absence and in the presence of the antagonist. A plot of Log DR-1 against Log D (the concentration of compound under test) is made and the point of intersection with the Log (DR-1) ordinate is taken as the measure of the activity ($pA_2$ value). The compounds of Examples 1 and 2 have $pA_2$ values greater than 8.

The histamine $H_2$-antagonist activity of the compounds of formula (1) can be determined in vitro in the guinea pig atrium test. In this test a spontaneously beating isolated portion of the guinea pig right atrium is secured under tension (300 mg,) between an anchorage and a transducer in a 15 ml tissue path and immersed in McEwens solution with constant aeration at a temperature of 37° C. The output from the transducer is amplified. Output is in turn fed to a flat bed recorder. Measured amounts of histamine are added to the tissue bath so that the histamine concentration increases step-wise until the rate of beating reaches a maximum. The tissue bath is washed out and filled with fresh McEwens solution containing compound under test. The solution is left in contact with the tissue for 60 min. and measured amounts of histamine are added again until a maximum rate is recorded. The assay is repeated with increasing concentrations of test compound and the dose of histamine giving 50% of maximum rate is noted. A dose ratio (DR) was calculated by comparing the concentrations of histamine required to product 50% maximum response in the absence and in the presence of the antagonist. A plot of Log DR-1 against Log D (the concentration of compound under test) is made and the point of intersection with the Log (DR-1) ordinate is taken as the measure of the activity ($pA_2$ value) The compounds of Examples 1 and 2 have ($pA_2$ values of less than 5.

The activity of compounds of formula (1) as histamine $H_1$-antagonists can be demonstrated in vivo by the inhibition of histamine induced bronchoconstriction. Guinea pigs of either sex anaesthetised by intraperitoneal injection of sodium pentobarbitone, 90 mg/kg. The trachea is cannulated. The animal is respired artificially with a fixed volume of air just adequate to inflate the lungs. The pressure needed to inflate the lungs is monitored from the respiratory system using a low pressure transducer. Intravenous injection of histamine causes dose-dependent increases in the pressure to inflate the lungs reflecting the bronchoconstrictor action of histamine. Responses to histamine can be antagonised using histamine $H_1$-receptor antagonists.

Dose-response curves to histamine are established at 20, 40, 80, 160 and 320 nmols/kg. Antagonists are then administered by intravenous injection and 5 minutes later a new histamine dose-response curve is established increasing the doses of hist-mine as necessary. The effect of the antagonist can be quantified by the displacement, to the right, of the histamine dose-response curve, expressed as a dose-ratio. A series of doses of antagonists may be given to each animal allowing calculation of dose-ratios for each dose of antagonist.

The activity of the compounds of formula (1) as histamine $H_2$-antagonists can be determined in vivo by the inhibition of histamine-stimulated secretion of gastric acid from the lumen-perfused stomachs of rats anaesthetised with urethane. This procedure is referred to in Ash and Schild, Brit. J. Pharmac. Chemother., 27, 247 (1966).

In order to use the compounds of the invention as histamine $H_1$-antagonists, they can be formulated as pharmaceutical compositions on accordance with standard pharmaceutical procedure.

The invention also includes pharmaceutical compositions comprising a compound of formula (1) or a pharmaceutically acceptable salt thereof and a pharmaceutically acceptable carrier.

Compounds of formula (1) and their pharmaceutically acceptable salts can be administered topically or systemically.

Topical formulations for administration to the skin include lotions and creams. Topical formulations for administration to the respiratory tract include solutions for application via a nebulizer or as an aerosol, or a microfine insufflatable powder. The active ingredient in an insufflatable powder has a small particle size i.e. less than 50 microns and preferably less than 10 microns. The active material is co-presented with a solid carrier for example lactose which has a particle size of less than 50 microns.

Systemic administration can be achieved by rectal, oral or parenteral administration. A typical suppository formulation comprises the active compound with a binding agent and/or lubricating agent for example gelatine or cocoa butter or other low melting vegetable waxes or fats. Typical parenteral compositions consist of a solution or suspension of the active material in a sterile aqueous carrier of parenterally acceptable oil.

Compounds of formula (1) which are active when given orally can be formulated as syrups, tablets, capsules and lozenges. A syrup formulation generally consists of a suspension or solution of the compound in a liquid carrier for example ethanol, glycerine or water with a flavouring or colouring agent. Where the composition is in the form of a capsule, the solid in granular form optionally with a binding agent is encased in a gelatin shell. Where the composition is in the form of a tablet, any suitable pharmaceutical carrier routinely used for preparing solid formulations can be used. Examples of such carriers include magnesium stearate, starch, lactose, glucose, sucrose, and cellulose. Preferably the composition is in unit dose form for example a tablet, capsule or metered aerosol.

Where appropriate, bronchodilators and antiasthmatics for example sympathomimetic amines particularly isoprenaline, isoetharine, salbutamol, phenylephrine and ephedrine; xanthine derivative is particularly theophylline and aminophylline; and corticosteroids particularly prednisolone and adrenal stimulants particularly ACTH can be included.

Each dosage unit for oral administration contains preferably from 1 to 200 mg of a compound of formula (1) or a pharmaceutically acceptable salt thereof calculated as the free base.

The invention also provides a method of blocking histamine $H_1$-receptors which comprises administering to a subject an effective amount to block said receptors of a compound of formula (1) or a pharmaceutically acceptable salt thereof.

The compounds of formula (1) and their pharmaceutically acceptable salts will normally be administered to a subject in!a pharmaceutical composition as described above, for the treatment of rhinitis, hayfever, bronchial asthma of allergic eczema. An adult subject will receive an oral dose of between 15 mg and 400 mg and preferably between 15 mg and 200 mg or an intravenous, subcutaneous or intramuscular dose of between 1 mg and 50 mg, and preferably between 1 mg and 10 mg of a compound of formula (1) or a pharmaceutically acceptable salt thereof calculated as the free base, the composition being administered 1 to 4 times per day.

The following Examples illustrate the invention.

EXAMPLE 1

(a) A solution of 4-(5-bromo-3-methylpyrid-2-yl)-butylamine (7.29 g) and dimethyl cyanodithioimidocarbonate (7.3 g) in isopropanol (100 ml) were refluxed for 2 hrs. A solid crystallised from the reaction mixture and was filtered and recrystallised from isopropanol to yield N-cyano-N'-[4-(5-bromo-3-methylpyrid-2-yl)-butylamino]-S-methylisothiourea (10.4 g) m.p. 127°–8° C.

(b) Reaction of N-cyano-N'-[4-(5-bromo-3-methylpyrid-2-yl)-butylamino]-S-methylisothiourea (2.0 g) with 33% methylamine in ethanol (50 ml) at reflux temperature for 1 hour yielded N-cyano-N'-methyl-N''-[4-(5-bromo-3-methyl-pyrid-2-yl)-butyl]-guanidine.

EXAMPLE 2

Reacting the product of Example 1(a) with benzylamine under the same conditions as Example 1(b) gave N-cyano-N'-benzyl-N''-[4-(5-bromo-3-methylpyrid-2-yl)butyl]-guanidine m.p. 140°–141° C.

EXAMPLE 3

By the method of Example 1(b) N-cyano-N'-(2-phenyl-ethyl)-N''-[4-(5-bromo-3-methyl-pyrid-2-yl)-butyl]-guanidine m.p. 76°–8° was prepared from the produce of Example 1(a) and phenyl ethylamine.

EXAMPLE 4

By the method of Example 1(b) N-cyano-N'-(3-phenylpropyl)-N''-[4-(5-bromo-3-methylpyrid-2-yl)-butyl]-guanidine m.p. 72°–4° C. was prepared from the product of Example 1(a) and phenylpropylamine.

EXAMPLE 5

By the method of Example 1(b) N-cyano-N'-(pyrid-2-yl methyl)-N''-[4-(5-bromo-3-methylpyrid-2-yl)-butyl]-guanidine m.p. 125°-8° C. was prepared from the product of Example 1(a) and 2-aminomethyl pyridine.

EXAMPLE 6

By the method of Example 1(b) N-cyano-N'-(pyrid-3-yl-methyl)-N''-[4-(5-bromo-3-methylpyrid-2-yl)-butyl]-guanidine m.p. 140°-141° C. was prepared from the product of Example 1(a) and 3-aminomethyl pyridine.

EXAMPLE 7

By the method of Example 1(b) N-cyano-N'-(pyrid-4-yl-methyl)-N''-[4-(5-bromo-3-methylpyrid-2-yl)-butyl]-guanidine m.p. 147°-8° C. was prepared from the product of Example 1(a) and 4-aminomethyl pyridine.

EXAMPLE 8

By the method of Example 1(b) N-cyano-N'-(2-pyrid-2-ylethyl)-N''-[4-(5-bromo-3-methylpyrid-2-yl)-butyl]-guanidine m.p. 74°-5° C. was prepared from the product of Example 1(a) and 2-pyridyl-ethylamine.

EXAMPLE 9

A solution of 3,4-dimethoxy-1,2,5-thiadiazole-1-oxide (1.62 g) in methanol has reacted with a solution of 4-(5-bromo-3-methylpyrid-2-y)-butylamine (2.43 g) in methanol. After 2 hours at room temperature, the reaction was cooled to 0° C. and saturated by passing ammonia gas for 10 mins. After 1.5 hours the product (which precipitated) was filtered off and recrystallised from ethanol to yield 3-[4-(5-bromo-3-methylpyrid-2yl)-butylamino]-4-amino-1,2,5-thiadiazole-1-oxide (1.2 g) m.p. 188°-190° C.

EXAMPLE 10

Substituting benzylamine1 for ammonia in the method of Example 9 gave 3-[4-(5-bromo-3-methylpyrid-2-yl)butylamino]-4-benzylamino-1,2 5-thiadiazole-1-oxide m.p. 175°-6° C. after recrystallisation from methanol.

EXAMPLE 11

Substituting 3-pyridylmethylamine for ammonia in the method of Example 9 gave 3-[4-(5-bromo-3-methylpyrid-2-yl)butylamino]-4-(3-pyridylmethylamino)-1,2,5-thiadiazole-1-oxide m.p. 179°-80° C. after recrystallisation from ethanol.

EXAMPLE 12

4-[5-Bromo-3-methylpyrid-2-yl]butylamine (0.681 g) in methanol (15 ml) was added to 3,4-dimethoxy-1,2,5-thiadiazole 1,1-dioxide (0.5 g) in methanol (25 ml) over 25 mins at a temperature of 4°-6° C. Ammonia was bubbled through with stirring at 15° C. for 2 hrs. The stirring was continued for a further 1 hr the solution evaporated to dryness, and titurated with acetone. Recrystallisation from acetone (50 ml), gave 3-[4[5-bromo-3-methyl-pyrid-2-yl]-butylamino]4-amino-1,2,5-thiadiazole-1,1-dioxide as a white solid (0.3 g) m.p. 219°-20.5° C.

$C_{12}H_{16}BrN_5O_2S$:

Requires C, 38.5; H, 4.31; N, 18.71.
Found C, 38.60;H, 4.26; N, 18.48.

EXAMPLE 13

Fusion of 4-(5-bromo-3-methylpyrid-2-yl)-butylamine (1.399 g) and 3-methylthio-1,2,4 dihydrothiadiazine-1,1-dioxide (0.99 g) at 150°-160° C. for 3.5 hours, followed by chromatography in ethyl acetate on silica gel yielded 3-[4-(5-bromo-3-methylpyrid-2-yl)-butylamino]-1,2,4-dihydrothiadiazine-1,1 dioxide m.p. 158°-9° C.

EXAMPLE 14

Treatment of 1,2-dimethocycyclobut-1-ene-3,4-dione with 4-(5-bromo-3-methylpyrid-2-yl)-butylamine in dry ether at 0° C. followed by methylamine in ethanol and chromatography in chloroform on silica gel yielded 1-methylamino-2-[4-(5-bromo-3-methylpyrid-2-yl)-butylamino]-cyclobut-1-ene-3,4-diode m.p. 190°-191° C. after recrystallisation from acetonitrile.

EXAMPLE 15

Substituting benzylamine for methylamine in the method of Example 14 yielded 1-benzylamino-2-[4-(5-bromo-3-methylpyrid-2-yl)-butylamino]-cyclobut-1-ene-3,4-dione m.p. 199°-200° C.

EXAMPLE 16

Substituting 3-pyridylmethylamine for methylamine in the method of Example 14 yielded 1-(pyrid-3-ylmethyl-amino)-2-[4-(5-bromo-3-methylpyrid-2-yl)-butylamino]-cyclobut-1-ene,-3,4-dione m.p. 204°-5° C.

EXAMPLE 17

4-[5-Bromo-3-methylpyrid-2-yl]butylamine (1.20 g), pyridine (5 ml) and 2-methylthio-4-pyrimidone (0.56 g) were refluxed until the reaction had gone to completion. Addition of ether precipitated the product and the supernatant liquid was discarded. Water (25 ml) was added to the residue and gave a yellow solid (0.83 g) m.p. 99°-106° C. which was chromatographed on silica gel, eluting with chloroform-methanol. The product so obtained was recrystallised from iso-propyl alcohol to give 2-[4-(5-bromo-3-methylpyrid-2-yl)butylamino]-4-pyrimidone (0.265 g) m.p. 109°-13° C.

EXAMPLE 18

(a) A mixture of concentrated sulphuric acid (35 ml) and nitric acid (35 ml) was added dropwise with stirring to a chilled (5° C.) solution of 2-amino-5-bromopyridine (50.3 g) in concentrated sulphuric acid (240 ml) maintaining the temperature of the reaction mixture at 5°-6° C. throughout the addition. When the addition was complete, the reaction mixture was stirred for a further 1.0 hr. at 5°-8° C. and then warmed to 30° C. and allowed to stand for ca 18 hr.

Further concentrated nitric acid (35 ml) was added portionwise to the reaction mixture with stirring while maintaining the temperature at 30°-40° C. A portion (50 ml) of the solution was poured into hot (ca 70° C.) water (100 ml) with rapid stirring and this mixture was heated to 120° C. Gas evolved. When the evolution of gas ceased further portions (75 ml) of the reaction mixture were added maintaining the temperature at 120° C. When the additions were completed, the solution obtained was poured into ice (1 kg) and chilled in a salt/ice bath. Fine orange crystals formed which were removed by filtration and recrystallised from dimethylformamide/water to give 2-hydroxy-3-nitro-5-bromopyridine (23.5 g) m.p. 240°-243° C.

(b) A solution of 2-hydroxy-3-nitro-5-bromopyridine (23.4 g) in phosphoryl chloride (16 ml) was heated under reflux for 2.5 hr. The reaction mixture was poured into ice/water and a brown solid was produced which was removed by filtration. The solid was dissolved in chloroform, dried (MgSO₄) and decolourised by heating with charcoal for 30 min. The solvent was evaporated from the decolourised solution to yield a yellow solid (24.0 g) which was recrystallised from ether/petroleum ether (40°–60° C.) to yield 2-chloro-3-nitro-5-bromopyridine (19.4 g) m.p. 66°–68° C.

(c) A solution of 2-(2-cyanoethyl)malonic acid diethyl ester (24.2 g) in tetrahydrofuran (15 ml) was added to a suspension of sodium hydride (2.45 g) in tetrahydrofuran (30 ml) at 20° C under nitrogen. To this was added 2-chloro-3-nitro-5-bromopyridine (22 g) and the mixture so obtained was heated to 93°–95° C. A small amount of tetrahydrofuran was allowed to distil off. The mixture was heated under Reflux for 2.5 hr. The reaction mixture was poured into water and neutralised to pH 7 with concentrated hydrochloric acid. The aqueous phase was extracted with chloroform, dried (MgSO₄) decolourised with charcoal and filtered through a silica column. The chloroform eluant was evaporated to yield an oil which slowly crystallised The crystals were washed in petroleum ether (40°–60° C.) and dried to yield 4-(5-bromo-3-nitropyrid-2-yl)-4,4-bis(carbethoxy)butyronitrile (28 g) m.p. 58°–62° C.

(d) 4-(5-Bromo-3-nitropyrid-2-yl)-4,4-bis(carbethoxy)butyronitrile (21.8 g) was added to a mixture of aqueous sodium hydroxide solution (1M, 263.6 ml) and methanol (635 ml). The mixture so obtained was stirred for 18 hr. The mixture was acidified to pH 1.5 by addition of concentrated hydrochloric to acid and heated at 50° C. for 4.75 hr. The solution was neutralised to pH 7 with sodium hydroxide solution and the methanol removed by distillation. The aqueous solution remaining was extracted with chloroform to give an oil (11.2 g) which was chromatographed on a silica column with chloroform to give 5-bromo-3-nitro-2-(3-cyanopropyl) pyridine (9.6 g) as a yellow solid m.p. 73°–76° C.

(e) Raney nickel moist [with ethanol (34 g) was added to a suspension of finely divided 5-bromo-3-nitro-2-(3-cyanopropyl)pyridine (8.4 g) an ethanol (350 ml) under nitrogen. The mixture was cooled (10° C.) and a solution of hydrazine hydrate (2.34 ml) in ethanol (10 ml) was added maintaining the reaction temperature between 12°–15° C. The reaction mixture was allowed to warm to room temperature with constant stirring and hydrazine hydrate (15.5 ml) was added in portions (2.3 ml) in ethanol (3 ml) at regular intervals over 46 hr. Before each addition the reaction mixture was cooled to 15° C. After 23 hr. more Raney nickel (6 g) was added. The reaction was stopped after 47 hr. The catalyst was removed by filtering the reaction mixture through a pad of diatomaceous earth. Evaporation of the solvent yielded an oil (7.9 g) which was chromatographed on a silica column eluting with ethyl acetate/ethanol/0.880 ammonia 15:10:2 to give 3-amino-5-bromo-2-(4-aminobutyl)pyridine (4.0 g) as an oil.

(f) A solution of 3,4-dimethoxy-1,2,5-thiadiazole-1-oxide (0.995 g) in methanol (25 ml) was reacted with a solution of 3-amino-5-bromo-(4-aminobutyl)pyridine (1.5 g) in methanol (25 ml) at room temperature for 3 hours. The solvent was removed in vacuo and the residue was chromatographed on silica in ethanol to give an oil which was triturated with ether and recrystallised from ethanol/ether to give 3-[4-(3-amino-5-bromopyrid-2-yl) butylamino]-4-methoxy-1,2,5-thiadiazole-1-oxide (1.7 g) m.p. 118°–120° C. (g) Reaction of 3-[4-(3-amino-5-bromopyrid-2-yl)-4-methoxy-1,2,5-thiadiazole-1-oxide (0.56 g) with methanolic ammonia solution (50 ml) at room temperature overnight gave after chromatography on silica in chloroform and trituration with ether 3-[4-(3-amino-5-bromopyrid-2-yl)butylamino]-4-amino-1,2,5-thiadiazole-1-oxide (0.19 g) m.p. 105°–109° C.

EXAMPLE 19

Reaction of the product from Example 18(f) (0.56 g) with 3-pyridylmethylamine (0]5 g) in methanol (25 ml) gave after chromatography on silica in chloroform and trituration with ether 3-[4-(3-amino-5-bromopyrid-2-yl)-butylamino]-4-(3-pyridylmethylamino)-1,2,5-thiadiazole-1-oxide (0.45 g) m.p. 76°–79° C.]

EXAMPLE 20

Reaction of the product from Example 18(f) (0.56 g) with 4-pyridylmethylamine (05 g) in methanol (25 ml) for 22 hours gave 3-[4-(3-amino-5-bromopyrid-2-yl)butylamino]-4-(4-pyridylmethylamino)-1,2,5-thiadiazole-1-oxide (0.35 g) m.p. 63°–66° C.

EXAMPLE 21

4-(5-Bromo-3-aminopyrid-2yl)-butylamine (0.5 g) and 2-methylthio-4-pyrimidone (0.3 g) were refluxed together in pyridine (1.5 ml) for 19 hours. The solvent was removed in vacuo and the resulting oil re-evaporated twice with n-propanol to give an off-white solid (0.88 g), which was purified by chromatography on silica in ethylacetate/ethanol/0.880 ammonia 15:10:2giving an oil (0.49 g). This was crystallised from acetonitrile/water 9:1 to give 2-[4-(3-amino-5-bromopyrid-2-yl)butylamino]pyrimid-4-one (0.47 g) m.p. 130°–135° C. (softens 82°–84° C. dehydration).

EXAMPLE 22

4-(5-Bromo-3-methylpyrid-2-yl)-butylamine (0.73 g) and 3-methylthiobenzothiadiazine-1,1-dioxide (0.68 g) were fused at 130°–140° C. for 3 hours. The product was crystallised from acetonitrile to yield 3-[4-(5-bromo-3-methylpyrid-2-yl)-butylamino]benzothiadiazine-1,1-dioxide m.p. 187°–8° C.

What is claimed is:
1. A compound of formula (1)

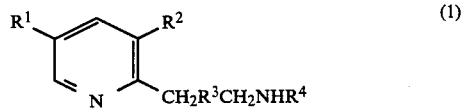

or a pharmaceutically acceptable salt thereof; where
R¹ is halogen, nitro, amino, C₁₋₄ alkylamino, C₁₋₄ alkanoylamino, or C₁₋₄ alkyl;
R² is halogen, nitro, amino, C₁₋₄ alkylamino, C₁₋₄ alkanoylamino, C₁₋₄ alkyl, or C₃₋₄ alkoxy;
R³ is a C₁₋₃ alkylene group; and
R⁴ is a group of formula (6):

where $R^{11}$ is hydrogen, $C_{1-6}$ alkyl, or phenyl or phenyl($C_{1-6}$) alkyl, unsubstituted or substituted with one or two $C_{1-6}$ alkyl or $C_{1-6}$ alkoxy groups or halogen atoms or a methylenedioxy group; pyridyl or pyridyl($C_{1-6}$)alkyl, unsubstituted or substituted with one $C_{1-6}$-alkyl group or $C_{1-6}$ alkoxy group or halogen atom.

2. A compound according to claim 1, where $R^1$ is halogen.

3. A compound according to claim 2, where $R^1$ is bromine.

4. A compound according to claim 1, where $R^2$ is $C_{1-4}$ alkyl.

5. A compound according to claim 4, where $R^2$ is methyl.

6. A compound according to claim 1, where $R^2$ is amino.

7. A hydrochloride salt of a compound of formula (1) according to claim 1.

8. A compound according to claim 1 which is 1-(pyrid-3-ylmethylamino)-2-[4-(5-bromo-3-methyl-pyrid-2-yl)-butylamino]-cyclobut-l-ene-3,4-dione; or a pharmaceutically acceptable salt thereof.

9. A pharmaceutical composition for blocking histamine $H_1$-receptors which comprises an effective amount of a compound according to claim 1 and a pharmaceutically acceptable carrier.

10. A method of blocking histamine $H_1$-receptors which comprises administering to a subject an effective amount to block said receptors of a compound according to claim 1.

* * * * *

UNITED STATES PATENT AND TRADEMARK OFFICE
CERTIFICATE OF CORRECTION

PATENT NO. : 4,863,936

DATED : September 5, 1989

INVENTOR(S) : George S. Sach

It is certified that error appears in the above-identified patent and that said Letters Patent is hereby corrected as shown below:

Column 1, line 64: "$C_{1-6}a$" should be -- $C_{1-6}$ alkyl -- .

Column 2, line 26: "$C_{-6}$" should be -- $C_{1-6}$ -- .

line 28: "($C_{-6,}$alkyl" should be -- "($C_{1-6}$)alkyl -- .

line 30: "$C_{-6}$alkyl" should be -- $C_{1-6}$ alkyl -- .

lines 31-32: delete "and $R^9$ or $C_{-6}$alkyl groups or halogen atoms;" .

line 50: "$C_{-6}$ alkoxy" should be -- $C_{1-6}$ alkoxy -- .

Column 3, line 37: "$R^2$ n-propoxy" should be -- $R^2$ are n-propoxy -- .

line 39: "$C_{-4}$ alkyl" should be -- $C_{1-4}$ alkyl -- .

line 52: "($C_{-6}$)" should be -- ($C_{1-6}$) -- .

Column 7, lines 66-68: delete "; line 26, change "U.K. patent application No. 2067987A" U.S. Pat. No. 4,374,248" .

Column 8, line 2: "U.K. Patent Application No. 2067987A" should be -- U.S. Patent No. 4,374,248 -- .

Column 10, line 61: "produce" should be -- product -- .

Column 11, line 36: "(1.2 g)" should be -- (1.12g) -- .

line 65: "$219°-20.5°$ C" should be -- $219-220.5°C$ -- .

UNITED STATES PATENT AND TRADEMARK OFFICE
CERTIFICATE OF CORRECTION

PATENT NO. : 4,863,936
DATED : September 5, 1989
INVENTOR(S) : George S. Sach

It is certified that error appears in the above-identified patent and that said Letters Patent is hereby corrected as shown below:

Column 12, line 17: "diode" should be -- dione -- .

line 43: "109°-13° C" should be -- 109-113°C -- .

Column 14, line 13: "(0]5 g)" should be -- (0.5 g) -- .

line 22: "(05 g)" should be -- 0.5 g) -- .

Signed and Sealed this

Twelfth Day of March, 1991

Attest:

HARRY F. MANBECK, JR.

Attesting Officer

Commissioner of Patents and Trademarks